US005476766A

United States Patent [19]
Gold et al.

[11] Patent Number: 5,476,766
[45] Date of Patent: Dec. 19, 1995

[54] LIGANDS OF THROMBIN

[75] Inventors: Larry Gold; Diane Tasset, both of Boulder, Colo.

[73] Assignee: Nexstar Pharmaceuticals, Inc., Boulder, Colo.

[21] Appl. No.: 973,333

[22] Filed: Nov. 6, 1992

Related U.S. Application Data

[63] Continuation-in-part of Ser. No. 714,131, Jun. 10, 1991, and a continuation-in-part of Ser. No. 536,428, Jun. 11, 1990, abandoned.

[51] Int. Cl.⁶ .............................. C12Q 1/68; C12P 19/34; C07H 21/02; C07H 21/04
[52] U.S. Cl. .............. 435/6; 435/91.2; 536/22.1
[58] Field of Search ................... 435/6, 91, 91.2; 536/22.1; 935/77, 78

[56] References Cited

U.S. PATENT DOCUMENTS 5,118,672  6/1992  Schinazi et al. .

FOREIGN PATENT DOCUMENTS

WO91/19813  12/1991  WIPO .
WO92/03568  3/1992  WIPO .

OTHER PUBLICATIONS

Bock et al., Nature 355:564–566 (Feb. 6, 1992).
Bar–Shavit et al. (1983) Science 220:728.
Bass and Cech (1984) Nature 308:820.
Berndt and Phillips (1981) in *Platelets in Biology and Pathology*, J. L. Gordon, ed. (Amsterdam:Elsevier/North–Holland Biomedical Press), pp. 43–74.
Carey et al. (1983) Biochemistry 22:2601.
Chen and Buchanan (1975) Proc. Natl. Acad. Sci. USA 72:131.
Chen et al. (1976) Exp. Cell Res. 101:41.
Daniel et al. (1986) J. Biol. Chem. 261:9579.
Eidt et al. (1989) J. Clin. Invest. 84:18.
Guschlbauer et al. (1977) Nucleic Acids. Res. 4:1933.
Hanson and Harker (1988) Proc. Natl. Acad. Sci. USA 85:3184.
Hattori et al. (1989) J. Biol. Chem. 264:7768.
Hobbs et al. (1973) Biochem. 12:5138.
Joyce (1989) in *RNA:Catalysis, Splicing, Evolution*, Belfort & Shub (Eds.) Elsevier, Amsterdam, pp. 83–87.
Kacian et al. (1972) Proc. Natl. Acas. Sci. USA 69:3038.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Marx (1992) Science 256:1278.
Mills et al. (1973) Science 180:916.
Mills et al. (1967) Proc. Nat.. Acad. Sci. USA 58:217.
Pieken et al. (1991) Science 253:314.
Rich et al. (1984) Ann. Rev. Biochem. 53:791.
Robertson and Joyce (1990) Nature 344:467.
Romaniuk et al. (1987) Biochemistry 26:1563.
Saffhill et al. (1970) J. Mol. Biol. 51:531.
Shibahara et al. (1987) Nucleic Acids. Res. 15:4403.
Schimmel (1989) Cell 58:9.
Tuerk et al. (1990) J. Mol. Biol. 213:749.
Tuerk et al. (1988) Proc. Natl. Acad. Sci. USA 85:1364.
Ulenbeck et al. (1983) J. Biomol. Structure Dynamics 1:539.
Vu et al. (1991) Cell 64:1057.
Witherell and Uhlenbeck (1989) Biochemistry 28:71.
Yarus (1988) Science 240:1751.
Zimmerman et al. (1986) Ann. N.Y. Acad. Sci. 485:349.

*Primary Examiner*—Stephanie W. Zitomer
*Attorney, Agent, or Firm*—Swanson & Bratschun

[57] ABSTRACT

Methods are described for the identification of nuclei acid ligand solutions to thrombin. The present invention utilizes the SELEX (Systematic Evolution of Ligands for EXponential enrichment) method for identifying and preparing RNA ligands to thrombin. Further included in the present invention are modified nucleotide sequences based on the sequences of the RNA ligands identified. The modified RNA ligands to thrombin exhibit increased in vivo stability.

9 Claims, 19 Drawing Sheets

| CLASS I | | 1 | 2 | 3 | SEQ ID NO: |
|---|---|---|---|---|---|
| | #1 | AGAUGCCUGUCGAGCAUGCUG | AGGAUCGAAGUAGUAGGCUUUGUGCUC | GUAGCUAAACAGCUUUGUCGACGGG | 4 |
| | #6 | AGAUGCCUGUCGAGCAUGCUG | AGGAUCGAAGUAGUAGGCUUUGUGCUC | GUAGCUAAACAGCUUUGUCGACGGG | 4 |
| | #13 | AGAUGCCUGUCGAGCAUGCUG | AGGAUCGAAGUAGUAGGCUUUGUGCUC | GUAGCUAAACAGCUUUGUCGACGGG | 4 |
| | #19 | AGAUGCCUGUCGAGCAUGCUG | AGGAUCGAAGUAGUAGGCUUUGUGCUC | GUAGCUAAACAGCUUUGUCGACGGG | 4 |
| | #23 | AGAUGCCUGUCGAGCAUGCUG | AGGAUCGAAGUAGUAGGCUUUGUGCUC | GUAGCUAAACAGCUUUGUCGACGGG | 4 |
| | #24 | AGAUGCCUGUCGAGCAUGCUG | AGGAUCGAAGUAGUAGGCUUUGUGCUC | GUAGCUAAACAGCUUUGUCGACGGG | 4 |
| | #25 | AGAUGCCUGUCGAGCAUGCUG | AGGAUCGAAGUUAGGCUUUGUGCUC | GUAGCUAAACAGCUUUGUCGACGGG | 4 |
| | #30 | AGAUGCCUGUCGAGCAUGCUG | AGGAUCGAAGUAGUAGGCUUUGUGCUC | GUAGCUAAACAGCUUUGUCGACGGG | 4 |
| | #2 | AGAUGCCUGUCGAGCAUGCUG | UACUGGAUCGAAGGAAGUAGGCAGUCAC | GUAGCUAAACAGCUUUGUCGACGGG | 5 |
| | #5 | AGAUGCCUGUCGAGCAUGCUG | AUAUCACGGAUCGAAGUAGGAAGUAGGCUG | GUAGCUAAACAGCUUUGUCGACGGG | 6 |
| | #9 | AGAUGCCUGUCGAGCAUGCUG | CCUUUCCCGGAUCGAAGUCAGUAGGCCGG | GUAGCUAAACAGCUUUGUCGACGGG | 7 |
| | #10 | AGAUGCCUGUCGAGCAUGCUG | CACCCGGAUCGAAGUAGUAGGCGUGAGU | GUAGCUAAACAGCUUUGUCGACGGG | 8 |
| | #15 | AGAUGCCUGUCGAGCAUGCUG | UGUACGGAUCGAAGGUAGUAGGCAGGUUAC | GUAGCUAAACAGCUUUGUCGACGGG | 9 |
| | #16 | AGAUGCCUGUCGAGCAUGCUG | CAUCCGGAUCGAAGUUAGUAGGCCGAGGUG | GUAGCUAAACAGCUUUGUCGACGGG | 10 |

FIG. 1-1

CLASS I (CONT'T)

| | 1 | 2 | 3 | SEQ ID NO: |
|---|---|---|---|---|
| #18 | AGAUGCCUGUCGAGCAUGCUG | AUUGUUGCGGAUCGAAGUGAGUAGGCGCUA | GUAGCUAAACAGCUUUGUCGACGGG | 11 |
| #21 | AGAUGCCUGUCGAGCAUGCUG | UGUACUGGAUCGAAGGUAGUAGGCAGUCAC | GUAGCUAAACAGCUUUGUCGACGGG | 12 |
| #22 | AGAUGCCUGUCGAGCAUGCUG | AUCGAAGUUAGUAGGAGCGUGUG | GUAGCUAAACAGCUUUGUCGACGGG | 13 |
| #26 | AGAUGCCUGUCGAGCAUGCUG | ACGCUGGAGUCGAAUCGAAAGGUAAGUAGGCGACU | GUAGCUAAACAGCUUUGUCGACGGG | 14 |
| #31 | AGAUGCCUGUCGAGCAUGCUG | GGGUCGGAUCGAAAGGUAAAGUAGGCGACU | GUAGCUAAACAGCUUUGUCGACGGG | 15 |
| #33 | AGAUGCCUGUCGAGCAUGCUG | AUAUCACGGAUCGAAAGAGUAGGCGU | GUAGCUAAACAGCUUUGUCGACGGG | 16 |
| #34 | AGAUGCCUGUCGAGCAUGCUG | UGUACUGGAUCGAAGGUAGUAGGCAC | GUAGCUAAACAGCUUUGUCGACGGG | 17 |
| #37 | AGAUGCCUGUCGDGCAUGCUG | AUAUCACGAUCGAAGGAAAGUAGGCGUG | GUAGCUAAACAGCUUUGUCGACGGG | 18 |

CLASS II

| | 1 | 2 | 3 | SEQ ID NO: |
|---|---|---|---|---|
| #3 | AGAUGCCUGUCGAGCAUGCUG | GUGCGGCUUUGGGCGCCGUGCUUGGC | GUAGCUAAACAGCUUUGUCGACGGG | 19 |
| #20 | AGAUGCCUGUCGAGCAUGCUG | GUGCGGCUUUGGGCGCCGUGCUUAC | GUAGCUAAACAGCUUUGUCGACGGG | 20 |
| #27 | AGAUGCCUGUCGAGCAUGCUG | GUGCGGCUUUGGGCGCCGUGCUUGAC | GUAGCUAAACAGCUUUGUCGACGGG | 21 |
| #35 | AGAUGCCUGUCGAGCAUGCUG | GGGCGGCUUUGGGCGCCGUGCUUGAC | GUAGCUAAACAGCUUUGUCGACGGG | 22 |
| #38 | AGAUGCCUGUCGAGCAUGCUG | GUGCGGCUUUUGGGCGCCGUGCUUGAC | GUAGCUAAACAGCUUUGUCGACGGG | 21 |
| #39 | AGAUGCCUGUCGAGCAUGCUG | GUGCGGCUUUGGGCGCCGUGCUUGAC | GUAGCUAAACAGCUUUGUCGACGGG | 21 |

FIG. 1-2

| CLONE | RANDOM REGION | SEQ ID NO: |
|---|---|---|
| 6 | gggagaugccuguc[g[agcaugcug AGGAUCGAAGUUAGUAGGCCUUUGUGUCU]C guagcuaaacagcuuugucgacggg | 23 |
| 16 | gggagaugccugucgagcau[gcug C[AU[CCGGAUCGAAGUUAGUAGGCCGAG]GUG guagcuaaacagcuuugucgacggg | 24 |
| 18 | gggagaugccugucgagcaugcug AUUGU[UGCGGGAUCGAAGUAGAGUAGGCGCUA] guagcuaaacagcuuugucgacggg | 25 |
| 27 | gggagaugccuguc[g[agcaugcug GUGCCGGCCUUUGGGCCCCGUGCUU]GAC guagcuaaacagcuuugucgacggg | 26 |

FIG. 2A

```
        AGUUA
       A     G U A G
       G  15 C-G U-U C G-U U-G C-U C G-C G U G
       C     -    - - - - - - - - - - -   - - -
       U     G    G A g u C g u a C g a g C u g u C g
       A
``` gggagaugc   cuaaacagcuuugucgacggg

CLONE 6

FIG. 2B-1 acgu = fixed region
ACGU = random region
ACGU = conserved region
―― = boundaries

```
                    G   U
         AGUUA    A   A
        A        G   G
        G    15  C - C
        C        G - C
        U        C - G
                 A     A
                 ─────────
                 C - G
                 U - G
                 A - U
                     G
                 C - g
                 g - u
                 u - a
                 c - g
                 g - c
``` gggagaugccugucgagcau — 24 — uaaacagcuuugucgacggg — 39 acgu = fixed region
ACGU = random region
ACGU = conserved region
───── = boundaries

CLONE 16

FIG. 2B-2

```
          AGUGA
         A     G
        G       U
        C   16  A
        U       G
         A     G
          G - C
          C - G
          G - C
              U
          U - A
          U - g
          G - u
          U - a
          U - g
gggagaugccugucgagcaugcugA    cuaaagagcuuugucgacggg
```

CLONE 18
FIG. 2B-3 acgu = fixed region
ACGU = random region
ACGU = conserved region
— = boundaries

```
                    G G C
              G  U   G C
         GGCUU    G C
          C       C — C
          G  19   g — G
          U       u — U
          G       a — G
          g       c — C
          u       g — U
          C       a — U
                  g — G
                  c — G
                  u — A
                  g — C
                  u — g gggagaugcc        uagcuaaacagcuuugucgacggg
```

CLONE 27

FIG. 2B-4 acgu  = fixed region
ACGU  = random region
ACGU = conserved region
———   = boundaries

CLONE 27

Peptidase Activity-Cleavage of tripeptide p-nitroaniline substrate (S2238)

H-D-Phe-Pip-Arg-p-Nitroaniline + H$_2$O $\xrightarrow{\text{Thrombin}}$ H-D-Phe-Pip-Arg-OH + p-Nitroaniline Measure the OD at 405 for release of p-Nitroaniline

| | [Thrombin] | [RNA] | Inhibition (decrease in OD$_{405}$) |
|---|---|---|---|
| Class I RNA 16 | 10$^{-8}$M | 10$^{-8}$M | – |
| | 10$^{-8}$M | 10$^{-7}$M | – |
| | 10$^{-9}$M | 10$^{-8}$M | – |
| Class II RNA 27 | 10$^{-8}$M | 10$^{-8}$M | – |
| | 10$^{-8}$M | 10$^{-7}$M | – |
| | 10$^{-9}$M | 10$^{-8}$M | – |

FIG. 6A

Fibrinogen Clotting Assay

| Ligand plus purified human thrombin (2.5nM) | Clotting time (sec) for purified fibrinogen (0.25 mg/ml) |
|---|---|
| No RNA/DNA | 65 |
| Class I RNA 16 (30nM) | 117 |
| Class II RNA 27 (60nM) | 115 |
| DNA 15mer G15D (SEQ ID NO:189) | 270-330 |

FIG. 6B

LIGANDS OF THROMBIN

This application is a Continuation-in-Part of U.S. patent application Ser. No. 07/714,131, filed Jun. 10, 1991, entitled Nucleic Acid Ligands and U.S. patent application Ser. No. 07/536,428, filed Jun. 11, 1990, entitled Systematic Evolution of Ligands by Exponential Enrichment, now abandoned.

FIELD OF THE INVENTION

Described herein are methods for identifying and preparing ligands to thrombin. Also included are the specific ligands identified pursuant to such methods. Specifically, RNA ligands are described to thrombin. The method utilized herein for identifying such RNA ligands is called SELEX, an acronym for Systematic Evolution of Ligands by EXponential enrichment. Also included within the scope of this invention are modified RNA ligands and mimetic ligands that are informed by the RNA ligands identified herein.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The Central Dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, are thought to have narrower chemical possibilities than proteins, but to have an informational role that allows genetic information to be passed from virus to virus, cell to cell, and organism to organism. In this context nucleic acid components, the nucleotides, possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is rather smaller. From the known examples of double-stranded DNA binding proteins, it has become possible to describe some of the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from E. coli. There are more known instances of target proteins that bind to single-stranded RNA ligands, although in these cases the single-stranded RNA often forms a complex three-dimensional shape that includes local regions of intramolecular double-strandedness. The amino-acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose functions is to inactivate ribosomes in a target organism. A family of evolutionary related RNAs binds with specificity and decent affinity to nucleotides and nucleosides (Bass, B. and Cech, T. (1984) Nature 308:820–826) as well as to one of the twenty amino acids (Yarus, M. (1988) Science 240:1751–1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated supra, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding (Uhlenbeck et al. (1983) J. Biomol. Structure Dynamics 1:539 and Romaniuk et al. (1987) Biochemistry 26:1563). It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of R17 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specificity.

Nucleic acids are known to form secondary and tertiary structures in solution. The double-stranded forms of DNA include the so-called B double-helical form, Z-DNA and superhelical twists (Rich, A. et al. (1984) Ann. Rev. Biochem. 53:791–846). Single-stranded RNA forms localized regions of secondary structure such as hairpin loops and pseudoknot structures (Schimmel, P. (1989) Cell 58:9–12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk, C. et al. (1988) Proc. Natl. Acad. Sci. USA 85:1364–1368).

A type of in vitro evolution was reported in replication of the RNA bacteriophage Qβ. Mills, D. R. et al. (1967) Proc. Natl. Acad. Sci USA 58:217–224; Levisohm, R. and Spiegelman, S. (1968) Proc. Natl. Acad. Sci. USA 60:866–872; Levisohm, R. and Spiegelman S. (1969) Proc. Natl. Acad. Sci. USA 63:805–811; Saffhill, R. et al. (1970) J. Mol. Biol. 51:531–539; Kacian, D. L. et al. (1972) Proc. Natl. Acad. Sci. USA 69:3038–3042; Mills, D. R. et al. (1973) Science 180:916–927. The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson (Joyce (1989) in RNA: Catalysis, Splicing, Evolution, Belfort and Shub (eds.), Elsevier, Amsterdam pp. 83–87; and Robertson and Joyce (1990) Nature 344:467) reported a method for identifying RNAs which specifically cleave single-stranded DNA. The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using a deoxyoligonucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants the variant that was most reactive for cleavage of a selected substrate.

The prior art has not taught or suggested more than a limited range of chemical functions for nucleic acids in their interactions with other substances: as targets for proteins that had evolved to bind certain specific oligonucleotide sequences; and more recently, as catalysts with a limited range of activities. Prior "selection" experiments have been limited to a narrow range of variants of a previously described function. Now, for the first time, it will be understood that the nucleic acids are capable of a vastly broad range of functions and the methodology for realizing that capability is disclosed herein.

U.S. patent application Ser. No. 07/536,428 filed Jun. 11, 1990, of Gold and Tuerk, entitled Systematic Evolution of Ligands by Exponential Enrichment, and U.S. patent application Ser. No. 07/714,131 filed Jun. 10, 1992 of Gold and Tuerk, entitled Nucleic Acid Ligands (See also PCT/US91/04078) describe a fundamentally novel method for making a nucleic acid ligand for any desired target. Each of these applications, collectively referred to herein as the SELEX Patent Applications, is specifically incorporated herein by reference.

The method of the SELEX Patent Applications is based on the unique insight that nucleic acids have sufficient capacity for forming a variety of two- and three-dimensional structures and sufficient chemical versatility available within their monomers to act as ligands (form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by a theory of preparation, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the method of the SELEX Patent Applications, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly effecting the affinity of the nucleic acid ligands to the target. By terminating the SELEX process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, Psuedoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20–50 nucleotides.

The SELEX Patent Applications also describe methods for obtaining nucleic acid ligands that bind to more than one site on the target molecule, and to nucleic acid ligands that include non-nucleic acid species that bind to specific sites on the target. The SELEX method provides means for isolating and identifying nucleic acid ligands which bind to any envisonable target. However, in preferred embodiments the SELEX method is applied to situations where the target is a protein, including both nucleic acid-binding proteins and proteins not known to bind nucleic acids as part of their biological function.

Thrombin is a multifunctional serine protease that has important procoagulant and anticoagulant activities. As a procoagulant enzyme thrombin clots fibrinogen, activates clotting factors V, VIII, and XIII, and activates platelets. The specific cleavage of fibrinogen by thrombin initiates the polymerization of fibrin monomers, a primary event in blood clot formation. The central event in the formation of platelet thrombi is the activation of platelets from the "nonbinding" to the "binding" mode and thrombin is the most potent physiologic activator of platelet aggregation (Berndt and Phillips (1981) in Platelets in Biology and Pathology, J. L. Gordon, ed. (Amsterdam:Elsevier/North Holland Biomedical Press), pp. 43–74; Hansen and Harker (1988) Proc. Natl. Acad. Sci. USA 85:3184–3188; Eidt et al. (1989) J. Clin. Invest. 84:18–27). Thus, as a procoagulant, thrombin plays a key role in the arrest of bleeding (physiologic hemostasis) and formation of vasoocclusive thrombi (pathologic thrombosis).

As an anticoagulant thrombin binds to thrombomodulin (TM), a glycoprotein expressed on the surface of vascular endothelial cells. TM alters substrate specificity from fibrinogen and platelets to protein C through a combination of an allosteric change in the active site conformation and an overlap of the TM and fibrinogen binding sites on thrombin. Activated protein C, in the presence of a phospholipid surface, $Ca^{2+}$, and a second vitamin K-dependent protein cofactor, protein S, inhibits coagulation by proteolytically degrading factors Va and VIIIa. Thus the formation of the thrombin-TM complex converts thrombin from a procoagulant to an anticoagulant enzyme, and the normal balance between these opposing activities is critical to the regulation of hemostasis.

Thrombin is also involved in biological responses that are far removed from the clotting system (reviewed in Zimmerman et al (1986) Ann. N. Y. Acad. Sci. 485:349–368; Marx (1992) Science 256:1278–1280). Thrombin is chemotactic for monocytes (Bar-Shavit et al. (1983) Science 220:728–730), mitogenic for lymphocytes (Chen et al. (1976) Exp. Cell Res. 101:41–46), mesenchymal cells (Chen and Buchanan (1975) Proc. Natl. Acad. Sci. USA 72:131–135), and fibroblasts (Marx (1992) supra). Thrombin activates endothelial cells to express the neutrophil adhesive protein GMP-140 (PADGEM) (Hattori et al. (1989) J. Biol. Chem. 264:7768–7771) and produce platelet-derived growth factor (Daniel et al. (1986) J. Biol. CHem. 261:9579–9582). Recently it has been shown that thrombin causes cultured nerve cells to retract their neurites (reviewed in Marx (1992) supra.

The mechanism by which thrombin activates platelets and endothelial cells is through a functional thrombin receptor found on these cells. A putative thrombin cleavage site (LDR/S) in the receptor suggests that the thrombin receptor is activated by proteolytic cleavage of the receptor. This cleavage event "unmasks" an N-terminal domain which then acts as the ligand, activating the receptor (Vu et al. (1991) Cell 64.:1057– 1068).

Vascular injury and thrombus formation represent the key events in the pathogenesis of various vascular diseases, including atherosclerosis. The pathogenic processes of the activation of platelets and/or the clotting system leading to thrombosis in various disease states and in various sites, such as the coronary arteries, cardiac chambers, and prosthetic heart valves, appear to be different. Therefore, the use of a platelet inhibitor, an anticoagulant, or a combination of both may be required in conjunction with thrombolytics to open closed vessels and prevent reocclusion.

Controlled proteolysis by compounds of the coagulation cascade is critical for hemostasis. As a result, a variety of complex regulatory systems exist that are based, in part, on a series of highly specific protease inhibitors. In a pathological situation functional inhibitory activity can be interrupted by excessive production of active protease or inactivation of inhibitory activity. Perpetuation of inflammation in response to multiple trauma (tissue damage) or infection (sepsis) depends on proteolytic enzymes, both of plasma cascade systems, including thrombin, and lysosomal origin. Multiple organ failure (MOF) in these cases is enhanced by the concurrently arising imbalance between proteases and their inhibitory regulators. An imbalance of thrombin activity in the brain may lead to neurodegenerative diseases.

Thrombin is naturally inhibited in hemostasis by binding to antithrombin III (ATIII), in a heparin-dependent reaction. Heparin exerts its effect through its ability to accelerate the action of ATIII. In the brain, protease nexin (PN-1) may be the natural inhibitor of thrombin to regulate neurite outgrowth.

Heparin is a glycosoaminoglycan composed of chains of alternating residues of D-glucosamine and uronic acid. Heparin is currently used extensively as an anticoagulant in the treatment of unstable angina, pulmonary embolism, atherosclerosis, thrombosis, and following myocardial infarction. Its anticoagulant effect is mediated through its interaction with ATIII. When heparin binds ATIII, the conformation of ATIII is altered, and it becomes a significantly enhanced inhibitor of thrombin. Although heparin is generally considered to be effective for certain indications, it is believed that the physical size of the ATIII.heparin complex prevents access to much of the biologically active thrombin in the body, thus diminishing its ability to inhibit clot formation. Side effects of heparin include bleeding, thrombocytopenia, osteoporosis, skin necrosis, alpe, hypersensitivity and hypoaldoseronism.

Hirudin is a potent peptide inhibitor of thrombin derived from the European medicinal leech Hirudis medicinalis. Hirudin inhibits all known functions of α-thrombin, and has been shown to bind thrombin at two separate sites kinetically; a high affinity site at or near the catalytic site for serine protease activity and a second anionic exosite. The anionic exosite also binds fibrinogen, heparin, TM and probably the receptor involved in mediating the activation of platelets and endothelial cells. A C-terminal hirudin peptide—which has been shown by co-crystallization with thrombin to bind in the anionic exosite—has inhibitory effects on fibrin formation, platelet and endothelial cell activation, and Protein C activation via TM binding, presumably by competing for binding at this site. This peptide does not inhibit proteolytic activity towards tripeptide chromogenic substrates, Factor V or X.

The structure of thrombin makes it a particularly desirable target for nucleic acid binding, due to the anionic exosite. Site-directed mutagenesis within this site has shown that fibrinogen-clotting and TM binding activities are separable. Conceivably, an RNA ligand could be selected that has procoagulatory and/or anticoagulatory effects depending on how it interacts with thrombin, i.e., which substrate it mimics.

A single stranded DNA ligand to thrombin has been prepared according to a procedure identical to SELEX. See, Bock et al. (1992) Nature 355:564–565. A consensus ligand was identified after relatively few rounds of SELEX were performed, that was shown to have some ability to prevent clot formation in vitro. The ligand is the 15mer DNA 5'GGTTGGTGTGGTTGG-3', referred to herein as G15D (SEQ ID NO:1). The symmetrical nature of the primary sequence suggests that G15D has a regular fixed tertiary structure. The kD of G15D to thrombin is about $2 \times 10^{-7}$. For effective thrombin inhibition as an anticoagulant, the stronger the affinity of the ligand to thrombin the better.

SUMMARY OF THE INVENTION

The present invention includes methods for identifying and producing nucleic acid ligands and the nucleic acid ligands so identified and produced.

Nucleic acid sequences are provided that are ligands to thrombin. More specifically, RNA sequences have been identified that are capable of binding to thrombin. Included within the invention are the nucleic acid ligand solutions shown in FIGS. 1 and 2.

Further included in this invention is a method of identifying nucleic acid ligands and ligand solutions to thrombin comprising the steps of a) preparing a candidate mixture of nucleic acids; b) partitioning between members of said candidate mixture on the basis of affinity to thrombin; and c) amplifying the selected molecules to yield a mixture of nucleic acids enriched for nucleic acid sequences with a relatively higher affinity for binding to thrombin.

More specifically, the present invention includes the RNA ligands to thrombin identified according to the above-described method, including those ligands listed in FIG. 1. Also included are RNA ligands to thrombin that are substantially homologous to any of the given ligands and that have substantially the same ability to bind to thrombin. Further included in this invention are RNA ligands to thrombin that have substantially the same structural form as the ligands presented herein and that have substantially the same ability to bind thrombin.

The present invention also includes modified nucleotide sequences based on the nucleic acid ligand solutions identified herein and mixtures of the same. Specifically included in this invention are RNA ligands, that have been modified at the ribose and/or phosphate and/or base positions to increase in vivo stability of the RNA ligand. Other modification to RNA ligands are encompassed by this invention, including specific alterations in base sequence, and additions of nucleic acids or non-nucleic acid moieties to the original compound.

BRIEF DESCRIPTION OF THE FIGURES

FIG. 1 depicts nucleotide sequences of RNA ligands isolated by SELEX for the human thrombin protein (Sigma). Each sequence is divided into 3 blocks from left to right: 1) the 5' fixed region, 2) the 30N variable region, and 3) the 3' fixed region. Individual sequences are grouped into class I and class II by conserved sequence motifs within the 30N variable region as indicated by bold, underlined characters.

FIG. 6 shows the results of functional assays of thrombin in the presence and absence of the RNA ligand inhibitors described. In A) the hydrolysis by thrombin of the chromogenic substrate S-2238 (H-D-Phe-Pip-Arg-pNitroaniline) at the indicated thrombin and RNA concentration was measured by the change in OD 405. In B) the conversion of fibrinogen to fibrin and resulting clot formation was measured by the tilt test in the presence and absence of the RNA ligand inhibitors described.

DETAILED DESCRIPTION OF THE PREFERRED EMBODIMENTS

Figures 2, 2B, 3, 4, 5:
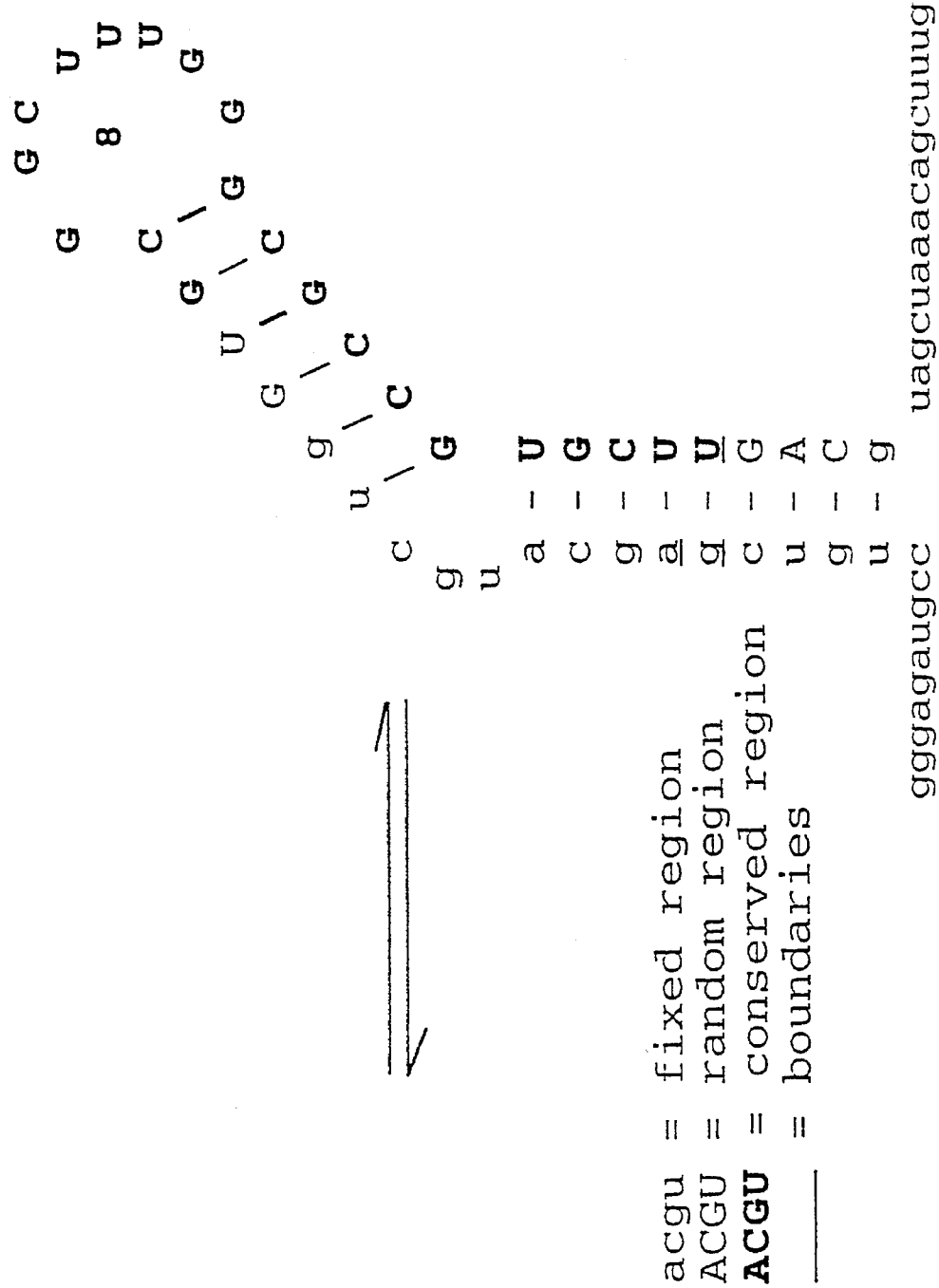
FIG. 2 shows proposed secondary structures of RNA ligands. (A) shows the sequence of the 76 nucleotide class I RNA clones 6, 16, and 18, and the class II 72 nucleotide clone 27. The boundary determinations where denotes a 5' boundary and ] denotes a 3' boundary are also shown. The possible secondary structures of each RNA are shown in (B) as determined from boundary experiments. Boundaries are underlined. In (A) and (B) the 5' and 3' fixed regions are depicted by small case lettering, the 30N random region by caps and the conserved region by bold caps. The hairpin structures that were synthesized are boxed with the total number of nucleotides indicated.
FIG. 3 depicts binding curves for thrombin ligands. In (A), RNAs with unique 30N3 sequence motifs (see FIG. 1) were chosen for binding analysis with human thrombin (Sigma), including the three from Class I: RNA 6, RNA 16, and RNA 18, and one from Class II: RNA 27. Binding of bulk RNA sequences of the 30N3 candidate mixture is also shown. In (B), binding of class I RNA clones 6, 16, 18 and class II RNA clone 27 is shown, but with human thrombin from Enzyme Research Laboratories. In (C), binding of the 15mer ssDNA 5'-GGTTGGTGTGGTTGG-3' (G15D), (SEQ ID NO:1), the class I clone 16 hairpin structures (24R, 39D) and the class II clone 27 hairpin structure (33R) (see FIG. 2B) are shown under identical conditions as in (B). In the case of the RNA hairpin structures, R denotes RNA synthesis and D denotes transcription from a DNA template.
FIG. 4 depicts a binding comparison of RNA ligands between unmodified RNA and RNA with pyrimidines modified to contain the 2'-$NH_2$ ribose nucleotide. Binding comparisons of (A) bulk RNA 30N3 candidate mixture and 2-$NH_2$ modified 30N candidate mixture, (B) class I RNA 16 and 2-$NH_2$ modified RNA 16, and (C) class II RNA 27 and 2-$NH_2$ modified RNA 27 are shown.
FIG. 5 depicts the competition experiments between the 15mer ssDNA G15D and RNA hairpin ligands of this invention for binding to human thrombin. In A) concentration of the tracer G15D is equal to the concentration of protein at 1 μM. The competitors for binding include G15D itself, the 24 and 39 nucleotide RNA hairpin structures from class I RNA 16, and the 33 nucleotide RNA hairpin structure from class II RNA 27 (see FIG. 2B). Binding is expressed as the relative fraction G15D bound, which is the ratio of G15D binding with competitor to G15D binding without competitor. In B) the RNA 33 is the tracer and the concentration of the tracer is equal to the concentration of protein at 300 ηM. The competitors for binding include ssDNA G15D and RNA 24.

This application is an extension and an application of the method for identifying nucleic acid ligands referred to as SELEX. The SELEX method is described in detail in U.S. patent application Ser. No. 07/714,131 filed Jun. 10, 1991 entitled Nucleic Acid Ligands and 07/536,428 filed Jun. 11, 1990 entitled Systematic Evolution of Ligands by EXponential Enrichment. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5– 50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

SELEX delivers high affinity ligands of a target molecule. This represents a singular achievement that is unprecedented in the field of nucleic acids research. The present invention applies the SELEX procedure to a specific target, thrombin. In the Example section below, the experimental parameters used to isolate and identify the nucleic acid ligand solutions to thrombin are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all, situations it is preferred that the nucleic acid ligand have the highest possible affinity to the target.

In copending and commonly assigned U.S. patent application Ser. No. 07/964,624, filed Oct. 21, 1992, methods are described for obtaining improved nucleic acid ligands after SELEX has been performed. This application, entitled Methods of Producing Nucleic Acid Ligands is specifically incorporated herein by reference. Included in this application are the following methods relating to: Assays of ligand effects on target molecules; Affinity assays of the ligands; Information boundaries determination; Quantitative and qualitative assessment of individual nucleotide contributions to affinity via secondary SELEX, nucleotide substitution, and chemical modification experiments; and Structural determination. The present invention includes improvements to the nucleic acid ligand solution derived according to these procedures.

This invention includes the specific nucleic acid ligands shown in FIG. 1. The scope of the ligands covered by this invention extends to all ligands to thrombin identified according to the SELEX procedure. More specifically, this invention includes nucleic acid sequences that are substantially homologous to and that have substantially the same ability to bind thrombin as the specific nucleic acid ligands shown in FIG. 1. By substantially homologous, it is meant, a degree of primary sequence homology in excess of 70%, most preferably in excess of 80%. Substantially the same ability to bind thrombin means that the affinity is within two orders of magnitude of the affinity of the ligands described herein. It is well within the skill of those of ordinary skill in the art to determine whether a given sequence—substantially homologous to those specifically described herein— has substantially the same ability to bind thrombin.

A review of the proposed structural formations shown in FIG. 2 for the group I and group II ligands shows that sequences that have little or no primary sequence homology may still have substantially the same ability to bind thrombin. It can be assumed that the disparate sequences have a common structure that gives rise to the ability to bind to thrombin, and that each of the group I and group II sequence ligands is able to assume structures that appear very similar to the binding site of thrombin even though they do not bind the same site. For these reasons, the present invention also includes RNA ligands that have substantially the same structure as the ligands presented herein and that have substantially the same ability to bind thrombin as the RNA ligands shown in FIG. 2. "Substantially the same structure" includes all RNA ligands having the common structural elements of the sequences given in FIG. 1.

This invention also includes the ligands as described above, wherein certain chemical modifications have been made in order to increase the in vivo stability of the ligand or to enhance or mediate the delivery of the ligand. Examples of such modifications include chemical substitutions at the ribose and/or phosphate and/or base positions of a given RNA sequence. See, e.g., Cook et al. PCT Application WO 9203568; U.S. Pat. No. 5,118,672 of Schinazi et al.; Hobbs et al. Biochem. 12:5138 (1973); Guschlbauer et al. Nucleic Acids. Res. 4:1933 (1977); Shibahara et al. Nucl. Acids. Res. 15:4403 (1987); Pieken et al. Science 253:314 (1991), each of which is specifically incorporated herein by reference. Specifically included within the scope of this invention are RNA ligands of thrombin that contain 2'-$NH_2$ modifications of certain riboses of the RNA ligand.

The nucleic acid ligands and nucleic acid ligand solutions to thrombin described herein are useful as pharmaceuticals and as part of gene therapy treatments.

The concepts of vascular injury and thrombosis are important in the understanding of the pathogenesis of various vascular diseases, including the initiation and progression of atherosclerosis, the acute coronary syndromes, vein graft disease, and restenosis following coronary angioplasty.

The high-affinity thrombin binding RNA ligands of this invention may be expected to have various properties. These characteristics can be thought about within the context of the hirudin peptide inhibitors and the current understanding of thrombin structure and binding. Within this context and not being limited by theory, it is most likely that the RNA ligands are binding the highly basic anionic exosite. It is also likely that the RNA is not binding the catalytic site which has high specificity for the cationic arginine residue. One would expect the RNA ligands to behave in the same manner as the C-terminal Hirudin peptides. As such, they would not strongly inhibit small peptidyl substrates, but would inhibit fibrinogen-clotting, protein C activation, platelet activation, and endothelial cell activation. Given that within the anionic exosite the fibrinogen-clotting and TM-binding activities are separable, it is possible that different high-affinity RNA ligands may inhibit these activities differentially. Moreover, one may select for one activity over another in order to generate a more potent anticoagulant than procoagulant.

The SELEX process for identifying ligands to a target was performed using human thrombin as the target, and a candidate mixture containing 76 nucleotide RNAs with a 30 nucleotide region of randomized sequences. Following twelve rounds of SELEX, a number of the selected ligands were sequenced, to reveal the existence of two groups of sequences that had common elements of primary sequence.

A dramatic shift in binding of the RNA population was observed after 12 rounds of SELEX, when compared to the bulk 30N RNA. Sequencing of bulk RNA after 12 rounds also showed a non-random sequence profile. The RNA was reverse transcribed, amplified, cloned and the sequences of 28 individual molecules were determined (FIG. 1). Based on primary sequence homology, 22 of the RNAs were grouped as class I and 6 RNAs were grouped as class II. Of the 22 sequences in class I, 16 (8 of which were identical) contained an identical sequence motif GGAUCGAAG(N)$_2$AGUAGGC (SEQ ID NO:2), whereas the remaining 6 contained 1 or 2 nucleotide changes in the defined region or some variation in N=2 to N=5. This conserved motif varied in its position within the 30N region. In class II, 3 of the 6 RNAs were identical and all of them contained the conserved motif GCGGCUUUGGGCGC-CGUGCUU (SEQ ID NO:3), beginning at the 3rd nucleotide from the end of the 5' fixed region.

Three sequence variant RNA ligands from class I (6, 16, and 18) and one (27) from class II, identified by the order they were sequenced, were used for individual binding analysis. Class I RNAs were exemplified by clone 16 with a kD of approximately 30 ηM and the kD for the class II RNA clone 27 was approximately 60 ηM.

In order to identify the minimal sequence requirements for specific high affinity binding of the 76 nucleotide RNA which includes the variable 30N region flanked by 5' and 3' fixed sequence, 5' and 3' boundary experiments were performed. For 5' boundary experiments the RNAs were 3' end labeled and hydrolyzed to give a pool of RNAs with varying 5' ends. For the 3' boundary experiments, the RNAs were 5' end-labeled and hydrolyzed to give a pool of RNAs with varying 3' ends. Minimal RNA sequence requirements were determined following RNA protein binding to nitrocellulose filters and identification of labeled RNA by gel electrophoresis.

3' boundary experiments gave the boundaries for each of the 4 sequences shown in FIG. 2A. These boundaries were consistent at all protein concentrations. 5' boundary experiments gave the boundaries shown in FIG. 3 plus or minus 1 nucleotide, except for RNA 16 which gave a greater boundary with lower protein concentrations. Based on these boundary experiments, possible secondary structures of the thrombin ligands are shown in FIG. 2B.

Figure 3A:
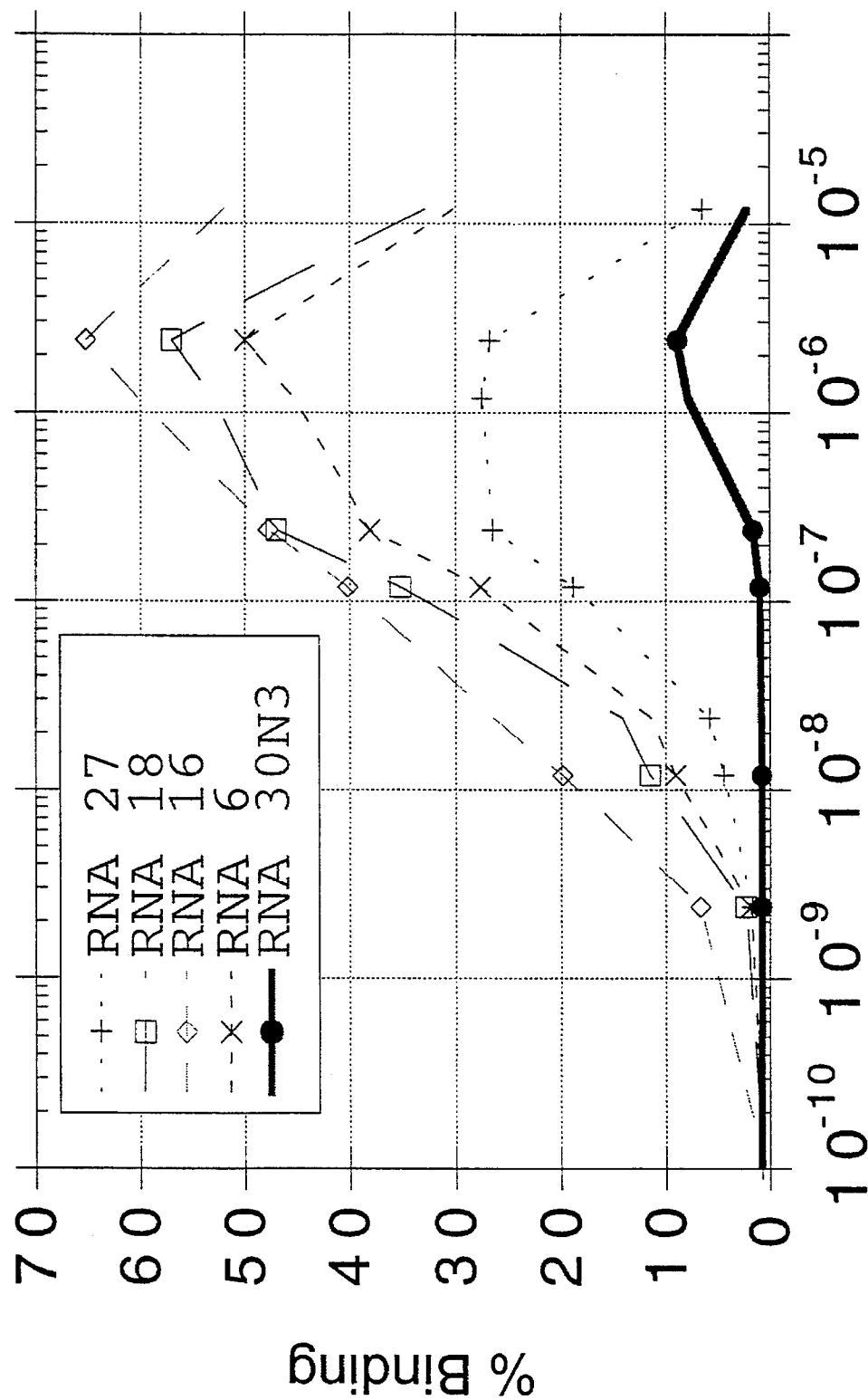
Figure 3B:
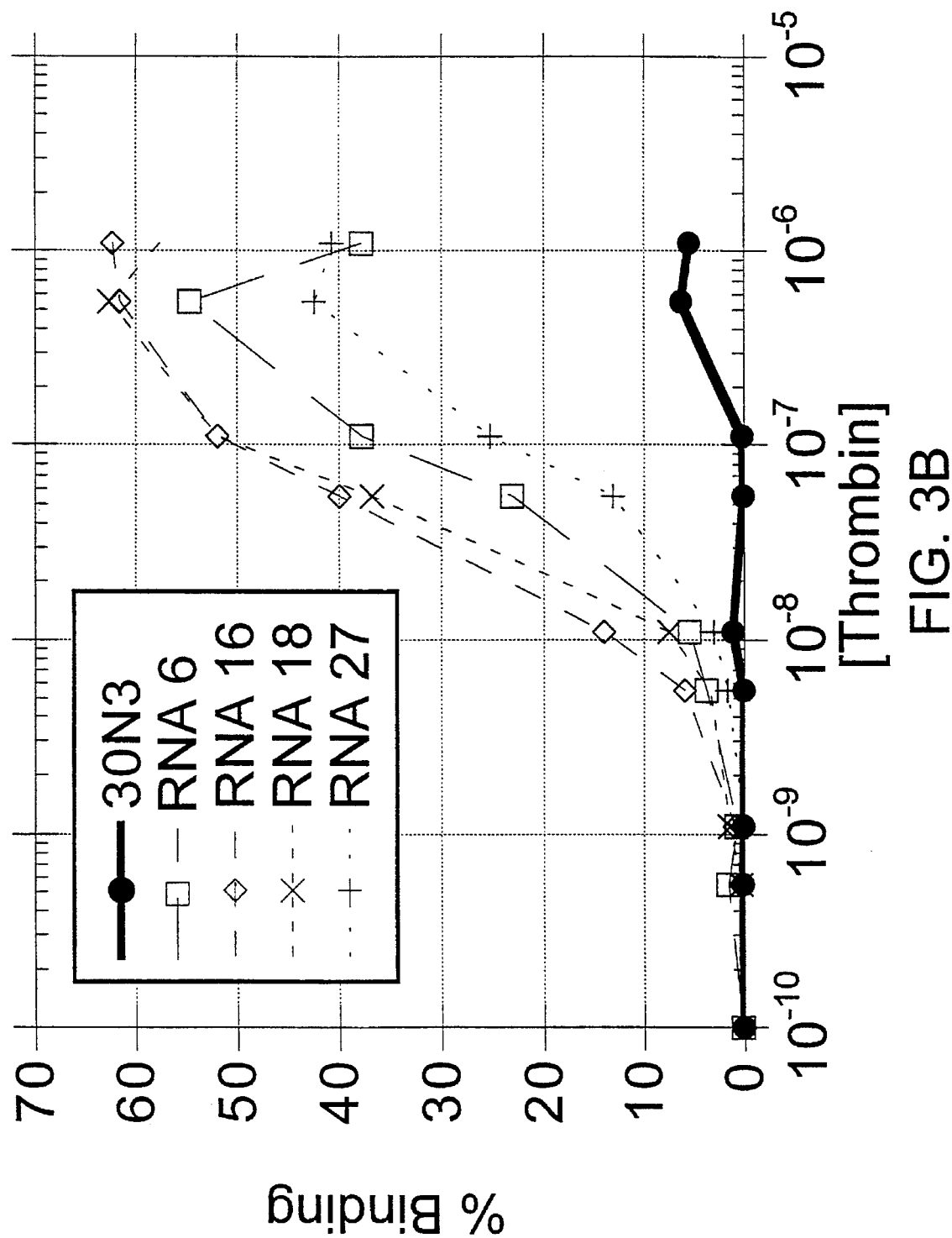
Figure 3C:
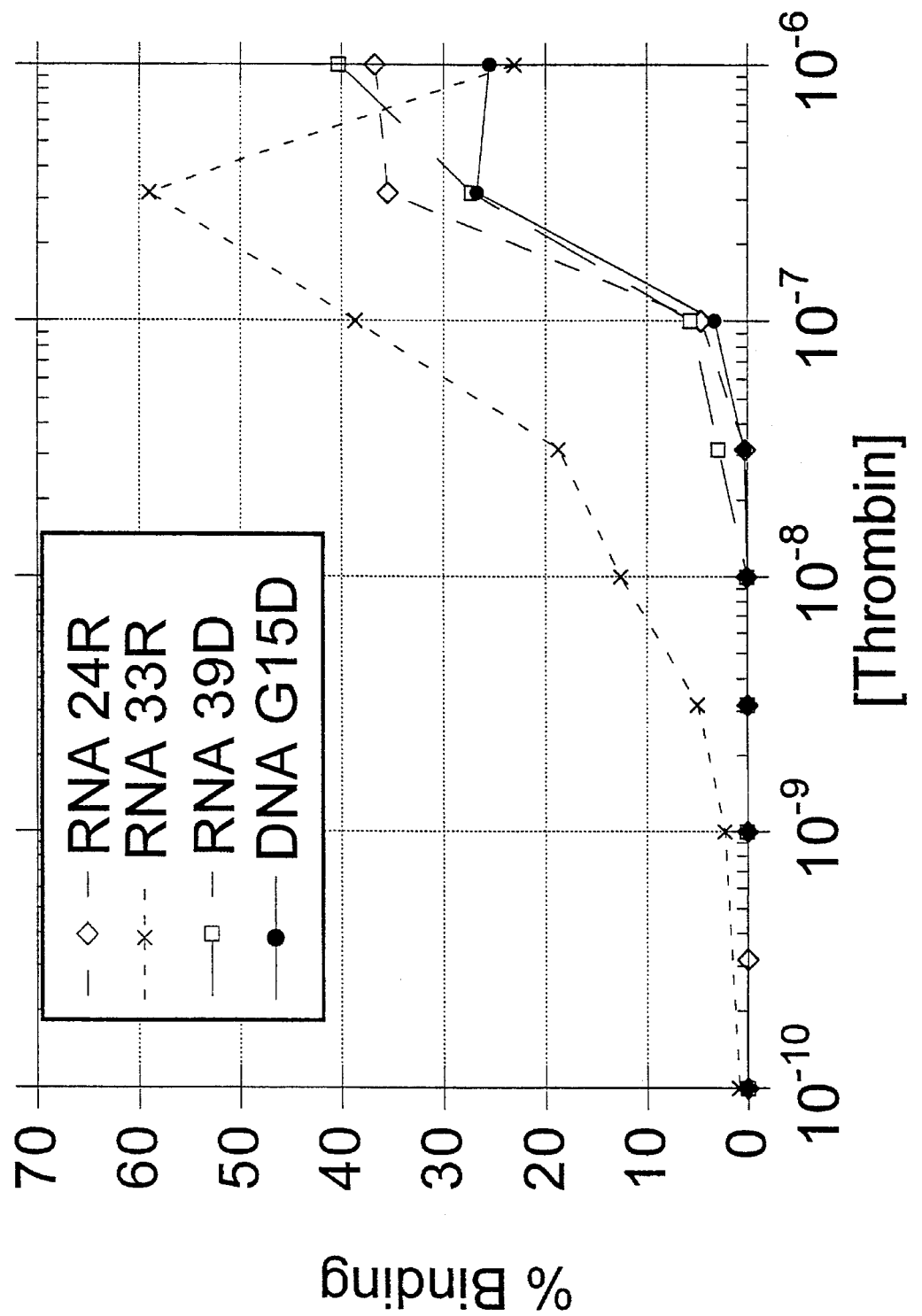
Figure 4A:
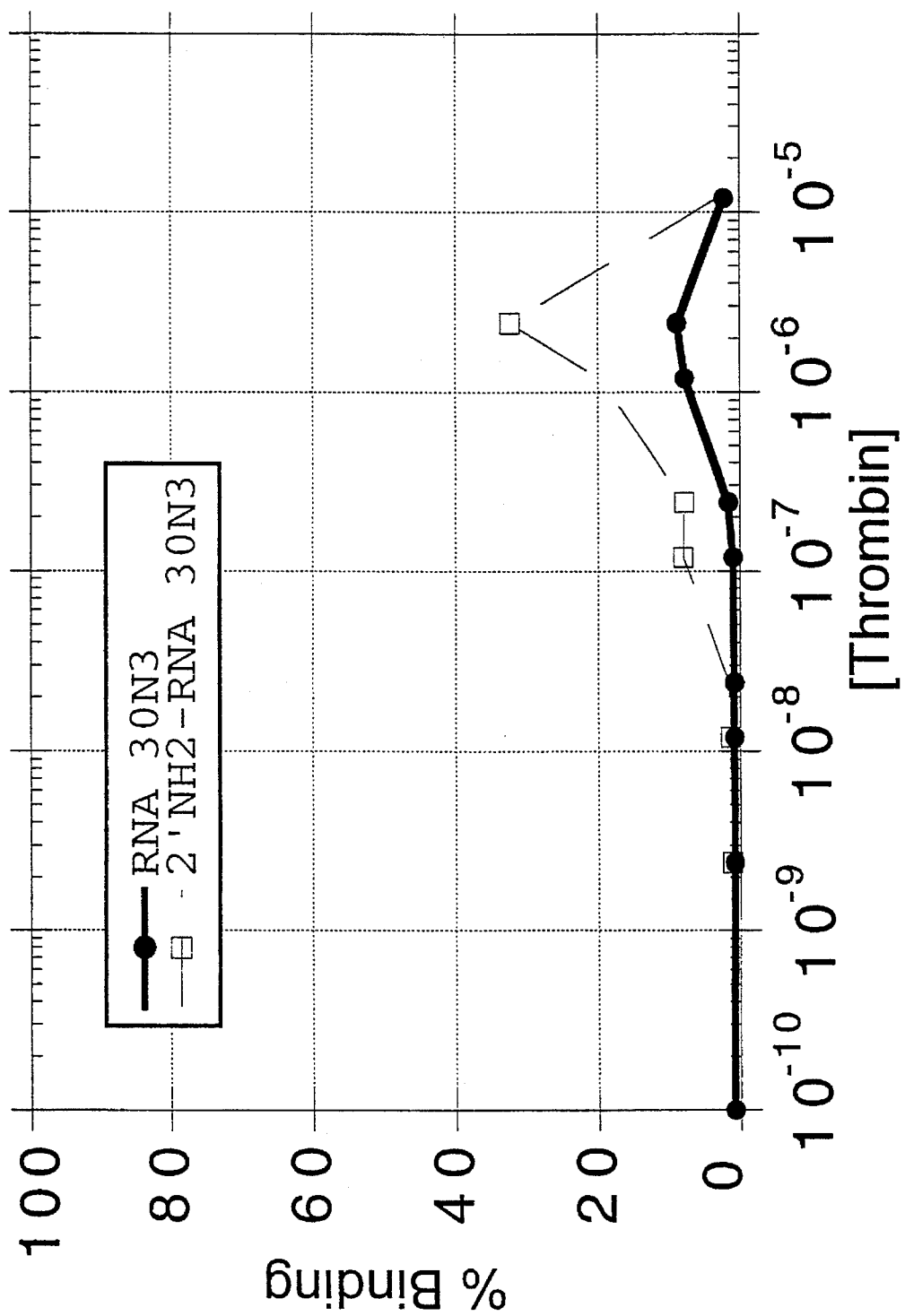
Figure 4B:
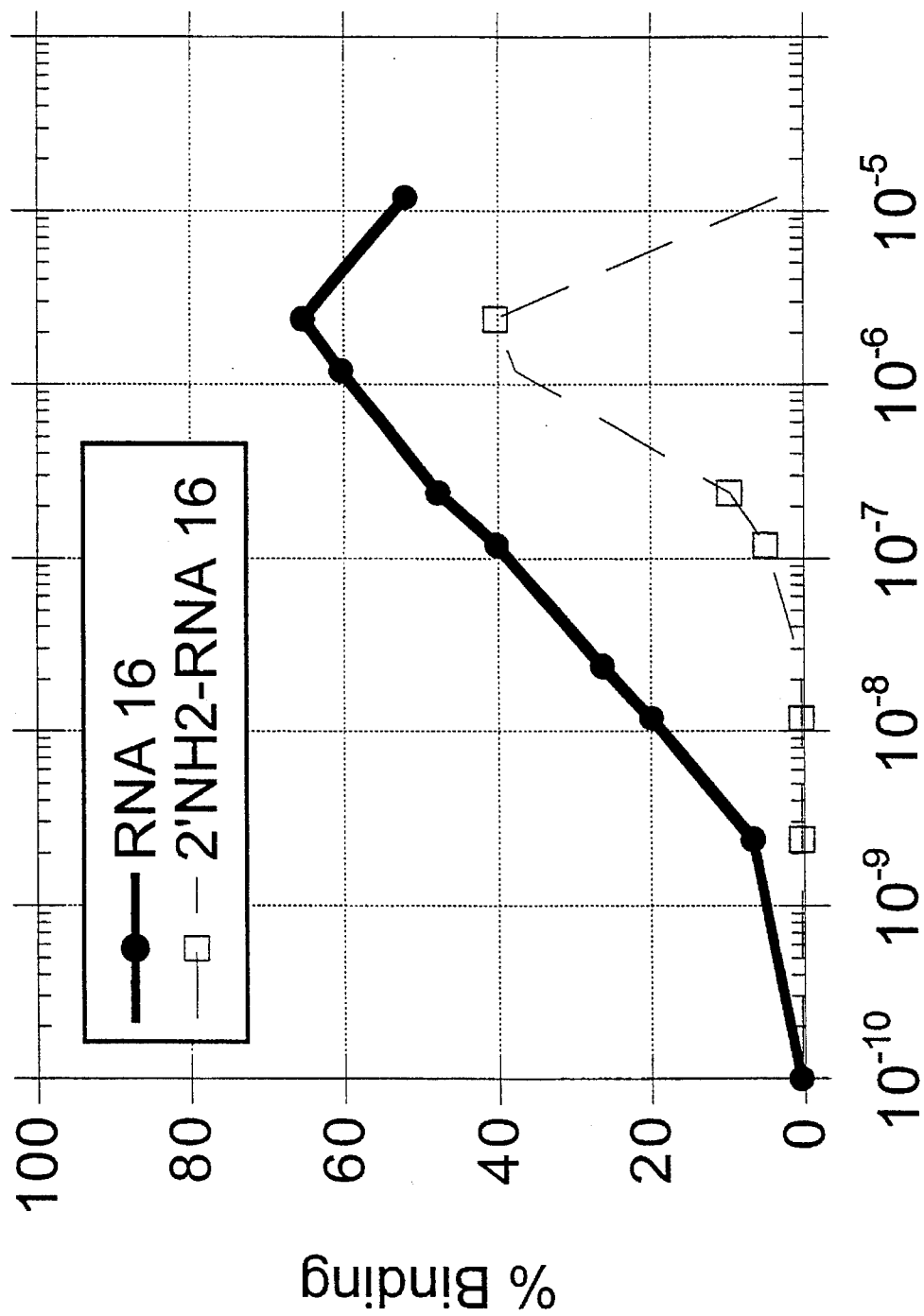
Figure 4C:
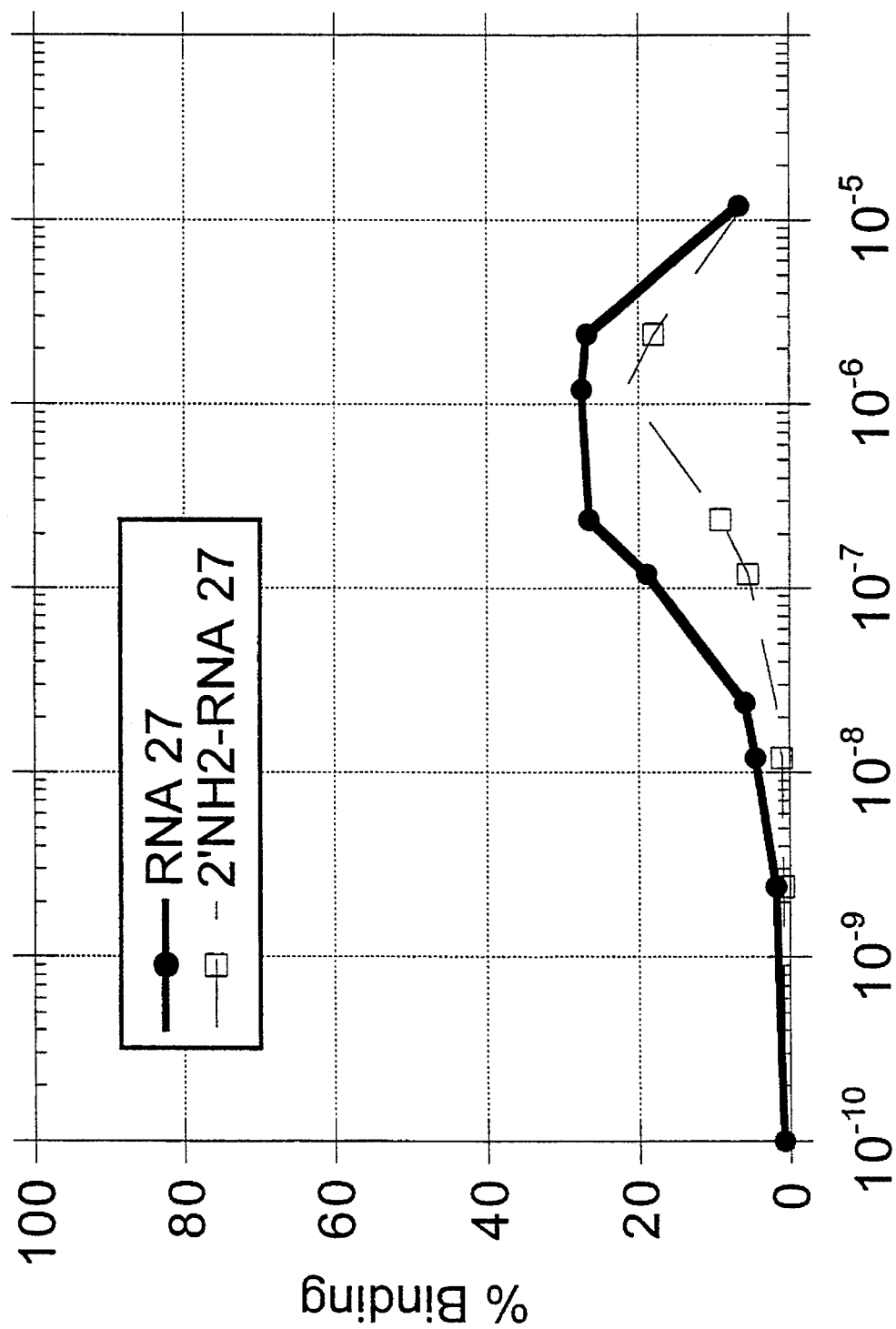
Figure 5A:
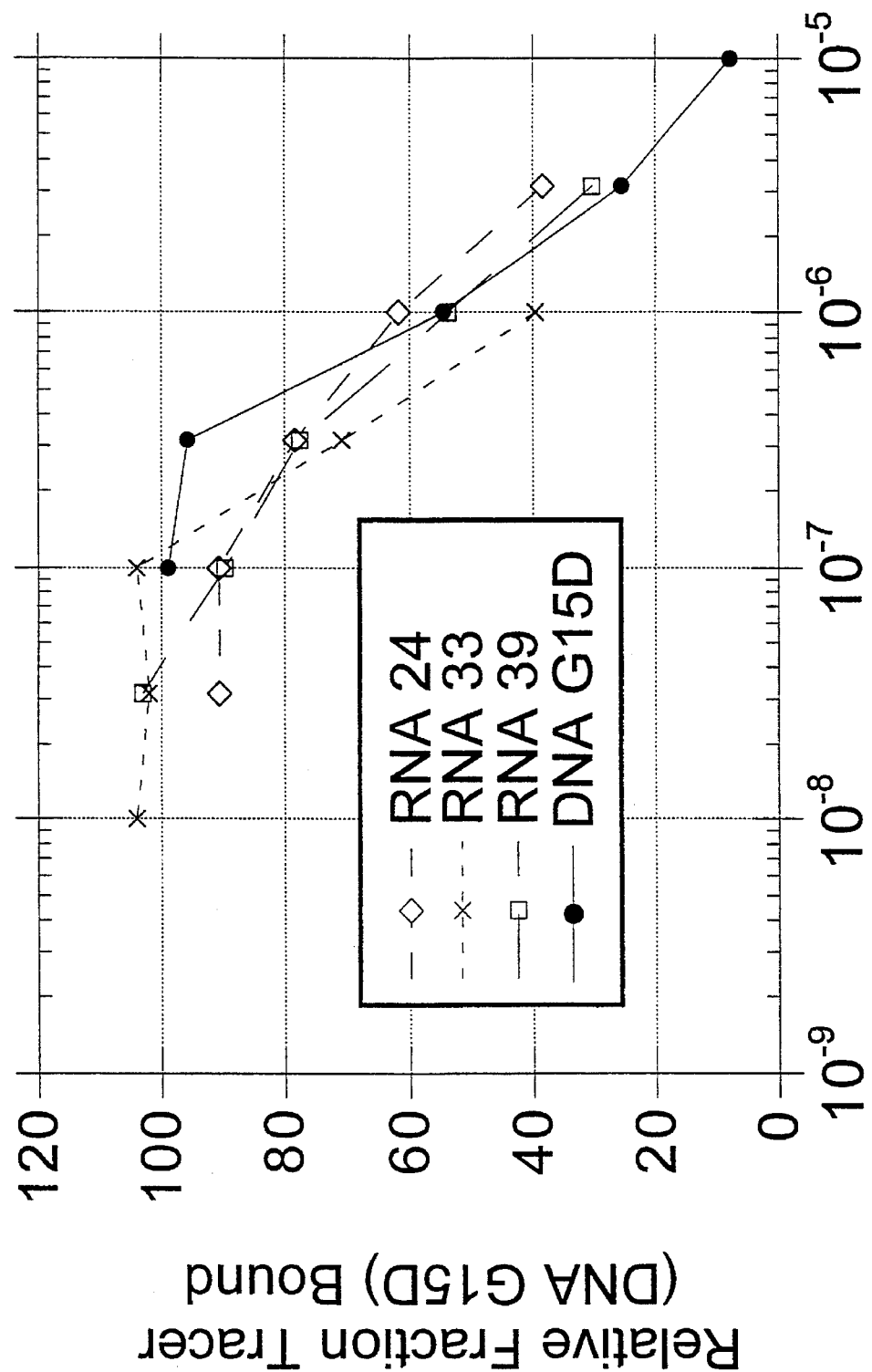
Figure 5B:
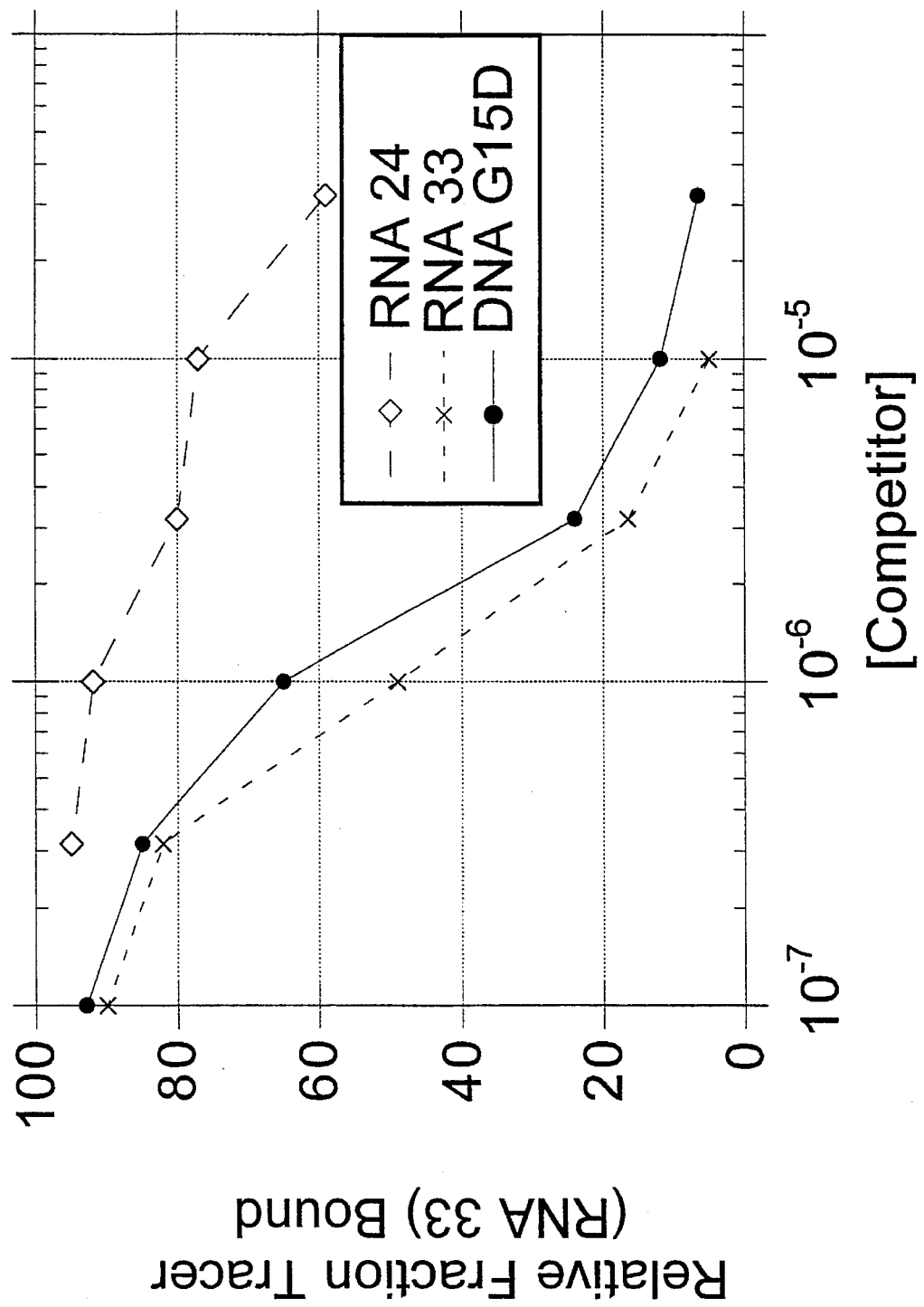

RNAs corresponding to the smallest and largest hairpin of class I clone 16 (24 and 39 nucleotides) and the hairpin of class II clone 27 (33 nucleotides) were synthesized or transcribed for binding analysis (see FIG. 2B). Results show that the RNA 27 hairpin binds with affinity (kD of about 60 ηM) equal to that of the entire 72 nucleotide transcript with fixed and variable region (compare RNA 27 in FIG. 3A with RNA 33R in FIG. 3C). The kDs for class I clone 16 RNA hairpins on the other hand increased an order of magnitude from 30 ηM to 200 ηM.

Modifications in the 2NH$_2$-ribose of pyrimidine residues of RNA molecules has been shown to increase stability of RNA (resistant to degradation by RNase) in serum by at least 1000 fold. Binding experiments with the 2NH$_2$-CTP/UTP modified RNAs of class I and class II showed a significant drop in binding when compared to the unmodified RNA (FIG. 4). Binding by the bulk 30N RNA, however, showed a slight increase in affinity when it was modified.

A ssDNA molecule with a 15 nucleotide consensus 5'-GGTTGGTGTGGTTGG-3' (G15D) (SEQ ID NO:1) has been shown to bind human thrombin and inhibit fibrin-clot formation in vitro (Bock et al. (1992) supra.). The results of competition experiments for binding thrombin between G15D and the RNA hairpin ligands of this invention are shown in FIG. 5. In the first of these experiments A), $^{32}$p-labeled G15D used as the tracer with increasing concentrations of unlabeled RNA or unlabeled G15D. As expected, when the G15D was used to compete for its own binding, binding of labeled DNA was reduced to 50% at equimolar concentrations (1 μM) of labeled and unlabeled competitor DNA. Both the class I clone 16 synthetic RNAs 24 and 39, and the class II clone 27 synthetic RNA 33 were able to compete for binding of G15D at this concentration. In B) the higher affinity class II hairpin RNA 33 (kD≈60 ηM) was $^{32}$P-labelled and used as the tracer with increasing concentrations of unlabelled RNA or unlabelled G15D DNA (kD≈200 ηM). In these experiments, the G15D was able to compete effectively with RNA 33 at higher concentrations than the RNA 33 competes itself (shift of binding to the right), which is what is expected when competing with a ligand with 3–4 fold higher affinity. The class II hairpin RNA 33 (kD≈ 60 ηM) was competed only weakly by the class I hairpin RNA 24 (kD≈200 ηM), suggesting that while there may be some overlap, the RNAs of these two classes bind with high affinity to different yet adjacent or overlapping sites. Because both of these RNAs can compete for G15D binding, this DNA 15mer probably binds in the region of overlap between the class I and class II hairpins.

Cleavage of Chromogenic Substrate S2238

The ability of thrombin to cleave the peptidyl chromogenic substrate S2238 (H-D-Phe-Pip-Arg-pNitroaniline) (H-D-Phe-Pip-Arg-pNA) (Kabi Pharmacia) was measured in the presence and absence of the RNA ligands of this invention. There was no inhibitory effect of RNA on this cleavage reaction at $10^{-8}$ M thrombin and $10^{-8}$ M RNA, $10^{-9}$ M thrombin and $10^{-8}$ M RNA or at $10^{-8}$ M thrombin and $10^{-7}$ M RNA (FIG. 6A). These results suggest that the RNA ligands do not bind in the catalytic site of the enzyme.

Cleavage of Fibrinogen to Fibrin and Clot Formation

The ability of thrombin to catalyze clot formation by cleavage of fibrinogen to fibrin was measured in the presence and absence of RNA. When RNA was present at a concentration equal to the Kd (30 ηM for class I RNAs and 60 ηM for class II RNAs), which was in 5 to 10-fold excess of thrombin, clotting time was increased by 1.5-fold (FIG. 6B).

Specificity of thrombin binding.

Figure 7A:
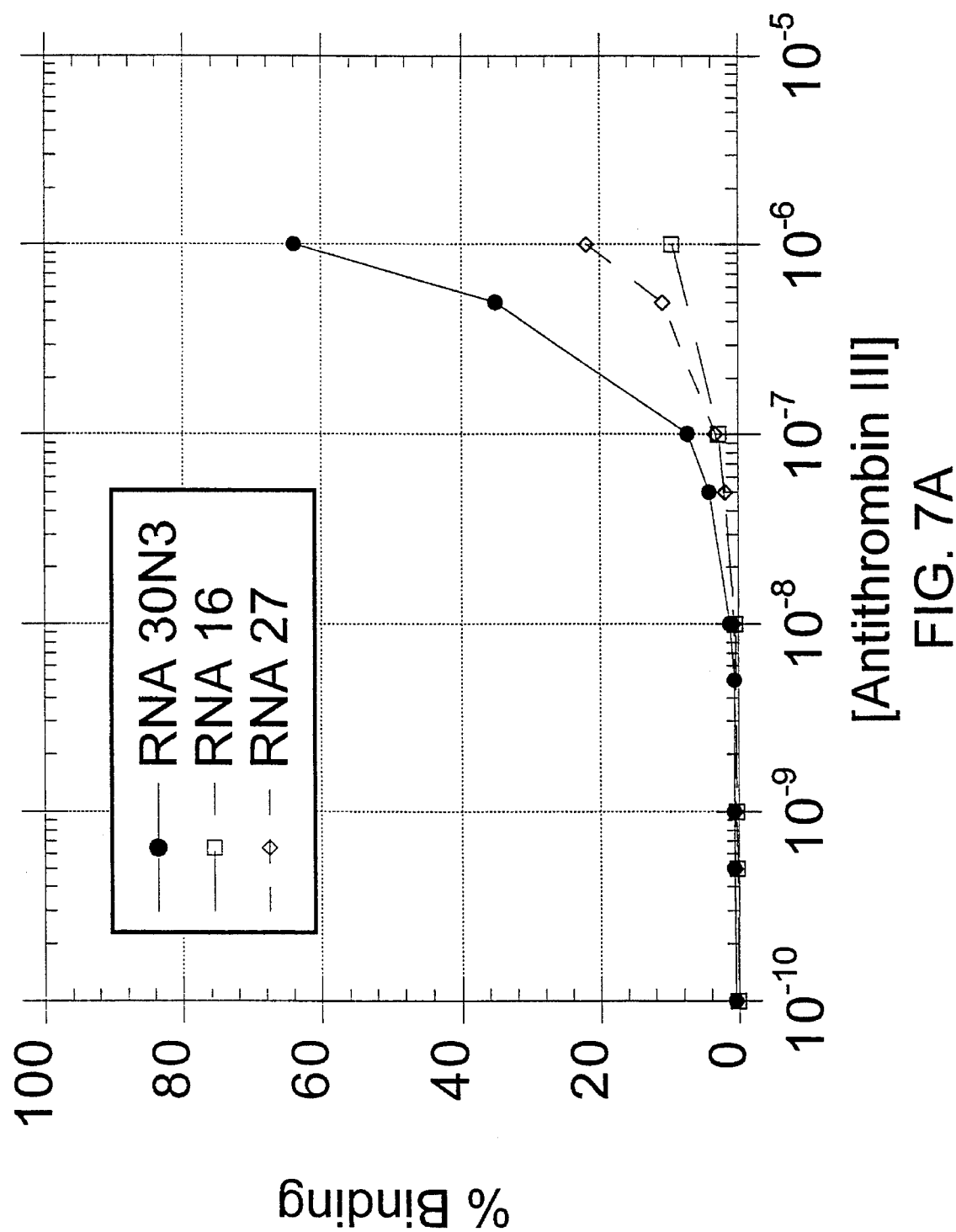
FIG. 7 shows specificity of binding for thrombin ligands. Class I RNA 16, class II RNA 27, and bulk 30N3 RNA were chosen for binding analysis with A) human antithrombin III (Sigma), and B) human prothrombin (Sigma).
Figure 7B:
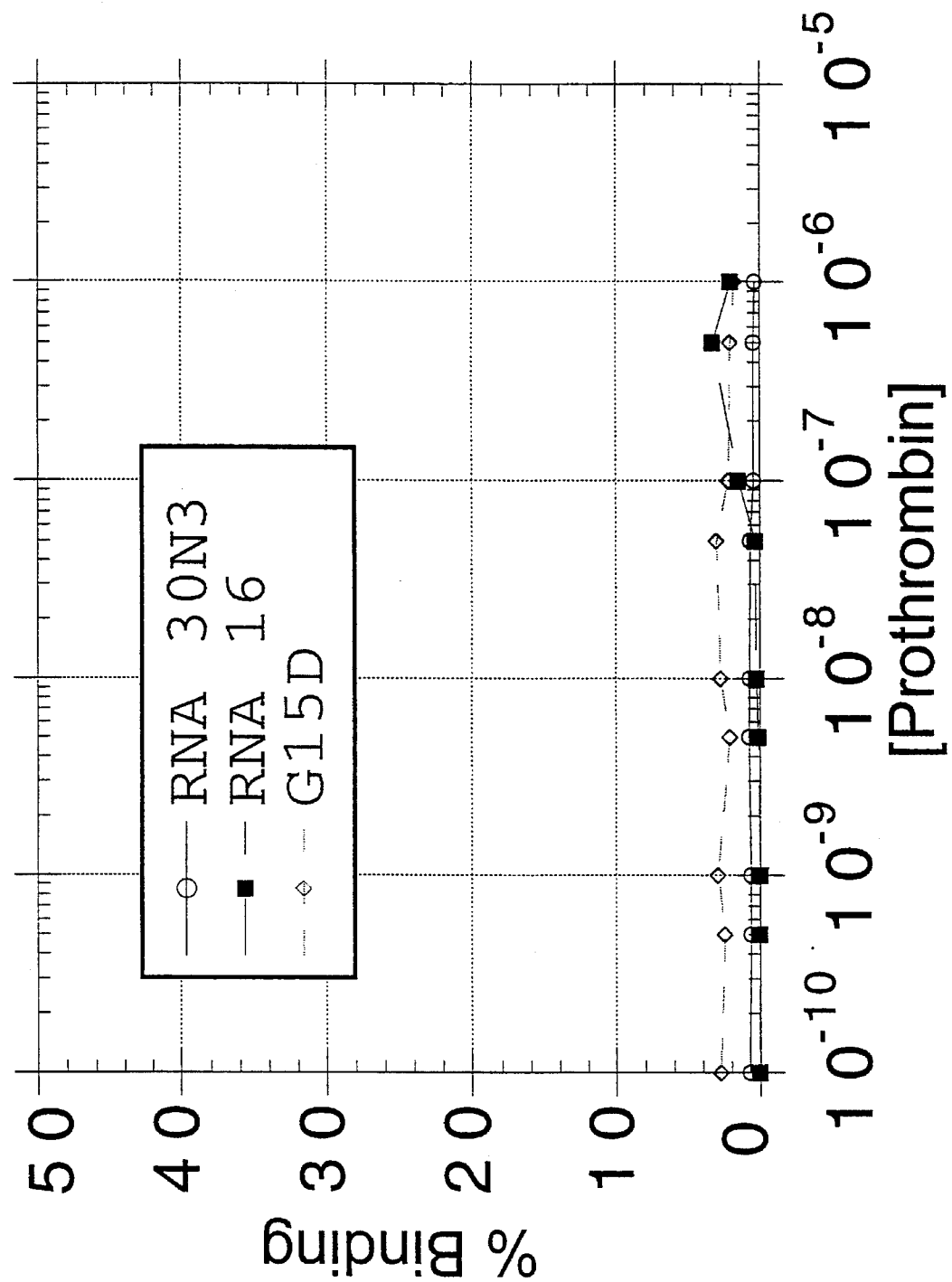

Representative ligands from class I and class II showed that these ligands had low affinity for ATIII at concentrations as high as 1 μM (FIG. 7A). These ligands showed reduced affinity when compared with the bulk 30N3 RNA suggesting that there has been selection against non-specific binding. This is of particular importance because ATIII is an abundant plasma protein with high affinity for heparin, a polyanionic macromolecule. These results show that the evolution of a discrete structure present in the class I and class II RNAs is specific for thrombin binding and, despite its polyanionic composition, does not bind to a high affinity heparin binding protein. It is also important to note that these thrombin specific RNA ligands have no affinity for prothrombin (FIG. 7B), the inactive biochemical precursor to active thrombin, which circulates at high levels in the plasma (≈1 μM).

Example I: Evolution of high affinity RNA ligands

High affinity RNA ligands for thrombin were isolated by SELEX. Random RNA molecules used for the initial candidate mixture were generated by in vitro transcription from a 102 nucleotide double-stranded DNA template containing a random cassette 30 nucleotides (30N) long. A population of $10^{13}$ 30N DNA templates was created by PCR, using a 5' primer containing the T7 promoter for in vitro transcription, and restriction sites in both the 5' and 3' primers for cloning.

The RNA concentration for each round of SELEX was approximately 2–4×10⁻⁷ M and concentrations of thrombin (Sigma, 1000 units) went from $1.0 \times 10^{-6}$ in the 1st round to $4.8 \times 10^{-7}$ in rounds 2 and 3 and $2.4 \times 10^{-7}$ in rounds 4–12. The binding buffer for the RNA and protein was 100 mM NaCl, 50 mM Tris/Cl, pH7.7, 1 mM DTT, and 1 mM $MgCl_2$. Binding was for 5 minutes at 37° C. in a total volume of 100 µl in rounds 1–7 and 200 µl in rounds 8–12. Each binding reaction was filtered through a pre-wetted (with 50 mM Tris/Cl, pH7.7) nitrocellulose filter (2.5 cm Millipore, 0.45 µM) in a Millipore filter binding apparatus, and immediately rinsed with 5 ml of the same buffer. The RNA was eluted from the filters in 400 µl phenol (equilibrated with 0.1M NaOAc pH5.2), 200 µl freshly prepared 7M urea as described (Tuerk et al. (1990) J. Mol. Biol. 213:749–761. The RNA was precipitated with 20 µg tRNA, and was used as a template for cDNA synthesis, followed by PCR and in vitro transcription to prepare RNA for the subsequent round. The RNA was radio-labeled with $^{32}p$-ATP in rounds 1–8 so that binding could be monitored. In order to expedite the time for each round of SELEX, the RNA was not labeled for rounds 9–12. RNA was prefiltered through nitrocellulose filters (1.3 cm Millipore, 0.45 µM) before the 3rd, 4th, 5th, 8th, 11th, and 12th rounds to eliminate selection for any nonspecific nitrocellulose binding.

Binding curves were performed after the 5th, 8th, and 12th rounds to estimate changes in kD of the bulk RNA. These experiments were done in protein excess at concentrations from $1.2 \times 10^{-5}$ to $2.4 \times 10^{-9}$ M at a final RNA concentration of $2 \times 10^{-9}$ M. The RNA for these binding curves was labeled to high specific activity with $^{32}p$-ATP or $^{32}p$-UTP. Binding to nitrocellulose filters was as described for the rounds of SELEX, except that the filter bound RNA was dried and counted directly on the filters.

Example II: RNA Sequencing

Following the 12th round of SELEX, the RNA was sequenced with reverse transcriptase (AMV, Life Sciences, Inc.) using the $^{32}p$ 5' end-labeled 3' complementary PCR primer.

Example III: Cloning and Sequencing individual RNAs

RNA from the 12th round was reverse transcribed to DNA and amplified by PCR. Digestion at restriction enzyme sites in the 5' and 3' fixed regions were used to remove the 30N region which was subsequently ligated into the complementary sites in the E. coli cloning vector pUC18. Ligated plasmid DNA was transformed into JM103 cells and screened by blue/white colony formation. Colonies containing unique sequences were grown up and miniprep DNA was prepared. Double-stranded plasmid DNA was used for dideoxy sequencing with the Sequenase kit version 2.0 and $^{35}S$-dATP (Amersham).

Example IV: End-labeling RNA

For end-labeling, RNA transcribed with T7 polymerase was gel purified by UV shadowing. RNA was 5' end-labeled by dephosphorylating the 5' end with alkaline phosphatase 1 unit, for 30 minutes at 37° C. Alkaline phosphatase activity was destroyed by phenol:chloroform extraction. RNA was subsequently end-labeled with $\gamma^{32}p$-ATP in a reaction with polynucleotide kinase for 30 minutes at 37° C. RNA was 3' end-labeled with $(5'-^{32}p)pCp$ and RNA ligase, for 30 minutes at 37° C. 5' and 3' end-labeled RNAs were gel band purified on an 8%, 8M urea, polyacrylamide gel.

Example V: Determination of 5' and 3' boundaries 2 pmole RNA 3' or 5' end-labeled for the 5' or 3' boundary experiments, respectively were hydrolyzed in 50 mM $Na_2CO_3$ (pH9.0) and 1 mM EDTA in a 10 µl reaction for 10 minutes at 90° C. The reaction was stopped by adding ⅕ volume 3M NaOAc (pH5.2), and freezing at −20° C. Binding reactions were done at 3 protein concentrations, 40 nM, 10 nM and 2.5 nM, in 3 volumes (100 µl, 400 µl, and 1600 µl, such that the amount of protein was kept constant) containing 1X binding buffer and 2 pmoles RNA. Reactions were incubated for 10 minutes at 37° C., filtered through a pre-wet nitrocellulose membrane, and rinsed with 5 ml wash buffer. The RNA was eluted from the filters by dicing the filter and shaking it in 200 µl 7M urea and 400 µl phenol (pH 8.0) for 15 minutes at 20° C. After adding 200 µl $H_2O$, the phases were separated and the aqueous phase extracted once with chloroform. The RNA was precipitated with ⅕ volume 3M NaOAc, 20 µg carrier tRNA, and 2.5 volumes ethanol. The pellet was washed once with 70% ethanol, dried, and resuspended in 5 µl $H_2O$ and 5 µl formamide loading dye. The remainder of the alkaline hydrolysis reaction was diluted 1:10 and an equal volume of loading dye was added. To locate where on the sequence ladder the boundary existed, an RNase T1 digest of the ligand was electrophoresed alongside the alkaline hydrolysis reaction and binding reactions. The digest was done in a 10 µl reaction containing 500 fmoles end-labeled RNA and 10 units RNase T1 in 7M urea, 20 mM Na-citrate (pH 5.0) and 1 mM EDTA. The RNA was incubated 10 minutes at 50° C. without enzyme and then another 10 minutes after adding enzyme. The reaction was slowed by adding 10 µl loading dyes and incubating at 4° C. Immediately after digestion, 5 µl of each of the digest, hydrolysis, and 3 binding reactions were electrophoresed on a 12% sequencing gel.

Example VI: In vitro transcription of RNA 2-$NH_2$ ribose derivatives of UTP and CTP RNA was transcribed directly from the pUC18 plasmid miniprep dsDNA template with T7 RNA polymerase in a reaction containing ATP, GTP, $2NH_2$-UTP and $2NH_2$-CTP. For $^{32}p$-labeled RNA, $^{32}p$-ATP was included in the reaction. Unmodified RNAs were transcribed in a mixture containing ATP, GTP, UTP, and CTP.

Example VII: Synthesis of RNA

RNA molecules corresponding to lower limits of nucleotide sequence required for high affinity binding to thrombin as determined by the boundary experiments (FIG. 2B) were synthesized on an Applied Biosystems 394 DNA/RNA Synthesizer. These RNA molecules include the class I clone 16 hairpin structures of 24 nucleotides (24R) and 39 nucleotides (39R) and the class II clone 27 hairpin of 33 nucleotides (33R).

Example VIII: Binding of individual RNA molecules

Four DNA plasmids with unique 30N sequences were chosen for in vitro transcription. $^{32}p$-labelled RNA was transcribed with conventional nucleotides as well as with the 2-$NH_2$ derivatives of CTP and UTP. Binding curves with these individual RNAs could be established using the binding buffer and thrombin (1000 units, Sigma) concentrations from $1.0 \times 10^{-5}$ to $1.0 \times 10^{-10}$ M. Human α thrombin (Enzyme Research Laboratories, ERL) was also used to determine binding affinities of RNA at concentrations from $1.0 \times 10^{-6}$ to $1.0 \times 10^{-10}$ M.

Binding of the 5' end-labeled single stranded 15mer DNA 5'-GGTTGGTGTGGTTGG-3' (G15D) (SEQ ID NO:1) described by Bock et al. (1992) supra, was determined under the binding conditions described herein with ERL thrombin and compared to binding by the radiolabelled RNA hairpin structures described above.

Example IX: Competition Experiments

To determine whether the RNA ligands described can compete for binding of the DNA 15 mer G15D to thrombin, equimolar concentrations (1 μM) of thrombin and the 5' end labeled DNA 15 mer G15D were incubated under filter binding conditions (kD of approximately 200 ηM) in the presence and absence of 'cold' unlabeled RNA or DNA ligand at varying concentrations from 10 nM to 1 uM. In the absence of competition, RNA binding was 30%. The protein was added last so competition for binding could occur. The RNA ligands tested for competition were the class I clone 16 synthetic RNAs 24mer (24R) and 39mer hairpins (39R) and the class II 27 synthetic RNA 33mer (33R). Results are expressed as the relative fraction of G15D bound (G15 with competitor/G15 without competitor) vs. the concentration of cold competitor.

To determine whether class I RNAs can compete for binding with class II RNAs and to confirm the competition with the G15D DNA, equimolar concentrations (300 ηM) of thrombin and the 5' end-labelled class II RNA 33 hairpin were incubated under filter binding conditions in the presence or absence of 'cold' unlabelled RNA 24 or DNA G15D at varying concentrations from 100 ηM to 32 μM. Results are expressed as the relative fraction of RNA 33 bound (RNA 33 with competitor/RNA 33 without competitor) versus the concentration of cold competitor (FIG. 5).

Example X: Chromogenic assay for thrombin activity and inhibition by RNA ligands The hydrolysis by thrombin of the chromogenic substrate S-2238 (H-D-Phe-Pip-Arg-pNitroaniline [H-D-Phe-Pip-Arg-pNA]) (Kabi Pharmacia) was measured photometrically at 405 nm due to the release of pnitroaniline (pNA) from the substrate.

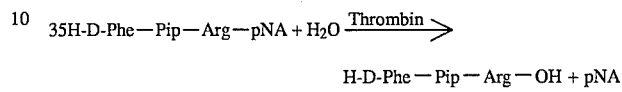

$$H\text{-}D\text{-}Phe - Pip - Arg - OH + pNA$$

Thrombin was added to a final concentration of $10^{-8}$ or $10^{-9}$ M to a reaction buffer (50 mM Na citrate, pH 6.5, 150 mM NaCl, 0.1% PEG), containing 250 μM S2238 substrate at 37° C. For inhibition assays, thrombin plus RNA (equimolar or at 10-fold excess) were preincubated 30 secs at 37° C. before adding to the reaction mixture (FIG. 6A).

Example XI: Fibrinogen Clotting

Thrombin was added for a final concentration of 2.5 nM to 400 μl incubation buffer (20 mM Tris-acetate, pH 7.4, 140 mM NaCl, 5 mM KCl, 1 mM $CaCl_2$, 1 mM $MgCl_2$) containing 0.25 mg/ml fibrinogen and 1 u/λ RNAse inhibitor (RNAasin, Promega) with or without 30 nM RNA class I or 60 ηM RNA class II at 37° C. Time in seconds from addition of thrombin to clot formation was measured by the tilt test (FIG. 6B).

Example XII: Specificity of Thrombin Binding

The binding affinity of the full-length class I RNA 16, class II RNA 27 and bulk 30N3 RNA for the serum proteins Antithrombin III (ATIII) and Prothrombin was determined by filter binding, as described above for the evolution of high affinity RNA ligands (Example I). These experiments were done in protein excess at concentrations from $1 \times 10^{-5}$ to $5 \times 10^{-10}$ M at a final RNA concentration of $2 \times 10^{-9}$ M (FIG. 7).

---

We claim:

1. A method for identifying nucleic acid ligands to thrombin comprising:
   a) preparing a candidate mixture of RNA nucleic acids;
   b) contacting the candidate mixture with thrombin, wherein RNA nucleic acids having an increased affinity to thrombin relative to the candidate mixture RNA nucleic acids may be partitioned from the remainder of the candidate mixture;
   c) partitioning the increased affinity RNA nucleic acids from the remainder of the candidate mixture; and
   d) amplifying the increased affinity nucleic acids, in vitro, to yield a ligand-enriched mixture of RNA nucleic acids, whereby RNA nucleic acid ligands to thrombin may be identified.

2. The method of claim 1 further comprising
   e) repeating steps b), c) and d).

3. The method of claim 1 wherein said candidate mixture of RNA nucleic acids is comprised of single stranded nucleic acids.

4. A nucleic acid ligand to thrombin identified according to the method of claim 1.

5. The nucleic acid ligand of claim 4 being a single stranded nucleic acid.

6. A purified and isolated non-naturally occurring RNA ligand to thrombin wherein the nucleotide sequence of said RNA ligand is selected from the group consisting of the nucleotide sequences set forth in FIG. 1.

7. The RNA ligand of claim 6 consisting of the nucleotide sequence (SEQ ID NO:2):

5'-GGAUCGAAG(N)$_2$AGUAGGC-3'

8. The RNA ligand of claim 6 consisting of having the nucleotide sequence (SEQ ID NO:3):

5'-GCGGCUUUGGGCGCCGUGCUU-3'

9. The RNA ligand of claim 6 identified by the method of claim 1.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGTTGGTGTG GTTGG        15

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGAUCGAANN AGUAGGC                                                                                      17

( 2 ) INFORMATION FOR SEQ ID NO:3:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

GCGGCUUUGG GCGCCGUGCU U                                                                                 21

( 2 ) INFORMATION FOR SEQ ID NO:4:

( i ) SEQUENCE CHARACTERISTICS:
    ( A ) LENGTH: 76 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

AGAUGCCUGU CGAGCAUGCU GAGGAUCGAA GUUAGUAGGC UUUGUGUGCU                                                   50

CGUAGCUAAA CAGCUUUGUC GACGGG                                                                            76

( 2 ) INFORMATION FOR SEQ ID NO:5:

( i ) SEQUENCE CHARACTERISTICS:
    ( A ) LENGTH: 74 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

AGAUGCCUGU CGAGCAUGCU GUACUGGAUC GAAGGUAGUA GGCAGUCACG                                                   50

UAGCUAAACA GCUUUGUCGA CGGG                                                                              74

( 2 ) INFORMATION FOR SEQ ID NO:6:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

AGAUGCCUGU CGAGCAUGCU GAUAUCACGG AUCGAAGGAA GUAGGCGUGG                                                   50

GUAGCUAAAC AGCUUUGUCG ACGGG                                                                             75

( 2 ) INFORMATION FOR SEQ ID NO:7:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

AGAUGCCUGU CGAGCAUGCU GCCUUUCCCG GGUUCGAAGU CAGUAGGCCG                                                   50

GGUAGCUAAA CAGUUUGUCG ACGGG                                                                             75

( 2 ) INFORMATION FOR SEQ ID NO:8:

( i ) SEQUENCE CHARACTERISTICS:

(A) LENGTH: 75 base pairs
(B) TYPE: nucleic acid
(C) STRANDEDNESS: single
(D) TOPOLOGY: linear (xi) SEQUENCE DESCRIPTION: SEQ ID NO:8:

| AGAUGCCUGU | CGAGCAUGCU | GCACCCGGAU | CGAAGUUAGU | AGGCGUGAGU | 50 |
| GUAGCUAAAC | AGCUUUGUCG | ACGGG | | | 75 |

(2) INFORMATION FOR SEQ ID NO:9:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:9:

| AGAUGCCUGU | CGAGCAUGCU | GUGUACGGAU | CGAAGGUAGU | AGGCAGGUUA | 50 |
| CGUAGCUAAA | CAGCUUUGUC | GACGGG | | | 76 |

(2) INFORMATION FOR SEQ ID NO:10:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:10:

| AGAUGCCUGU | CGAGCAUGCU | GCAUCCGGAU | CGAAGGUAGU | AGGCCGAGGU | 50 |
| CGUAGCUAAA | CAGCUUUGUC | GACGGG | | | 76 |

(2) INFORMATION FOR SEQ ID NO:11:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:11:

| AGAUGCCUGU | CGAGCAUGCU | GAUUGUUGCG | GAUCGAAGUG | AGUAGGCGCU | 50 |
| AGUAGCUAAA | CAGCUUUGUC | GACGGG | | | 76 |

(2) INFORMATION FOR SEQ ID NO:12:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (xi) SEQUENCE DESCRIPTION: SEQ ID NO:12:

| AGAUGCCUGU | CGAGCAUGCU | GUGUACUGGA | UCGAAGGUAG | UAGGCAGUCA | 50 |
| CGUAGCUAAA | CAGCUUUGUC | GACGGG | | | 76 |

(2) INFORMATION FOR SEQ ID NO:13:

(i) SEQUENCE CHARACTERISTICS:
        (A) LENGTH: 69 base pairs
        (B) TYPE: nucleic acid
        (C) STRANDEDNESS: single
        (D) TOPOLOGY: linear ( x i ) SEQUENCE DESCRIPTION: SEQ ID NO:13:

AGAUGCCUGU CGAGCAUGCU GAUCGAAGUU AGUAGGAGCG UGUGGUAGCU      50

AAACAGCUUU GUCGACGGG      69

( 2 ) INFORMATION FOR SEQ ID NO:14:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AGAUGCCUGU CGAGCAUGCU GACGCUGGAG UCGGAUCGAA AGGUAAGUAG      50

GCGACUGUAG CUAAACAGCU UUGUCGACGG G      81

( 2 ) INFORMATION FOR SEQ ID NO:15:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

AGAUGCCUGU CGAGCAUGCU GGGGUCGGAU CGAAAGGUAA GUAGGCGACU      50

GUAGCUAAAC AGCUUUGUCG ACGGG      75

( 2 ) INFORMATION FOR SEQ ID NO:16:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

AGAUGCCUGU CGAGCAUGCU GAUAUCACGG AUCGAAAGAG AGUAGGCGUG      50

UAGCUAAACA GCUUUGUCGA CGGG      74

( 2 ) INFORMATION FOR SEQ ID NO:17:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AGAUGCCUGU CGAGCAUGCU GUGUACUGGA UCGAAGGUAG UAGGCAGGCA      50

CGUAGCUAAA CAGCUUUGUC GACGGG      76

( 2 ) INFORMATION FOR SEQ ID NO:18:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AGAUGCCUGU CGDGCAUGCU GAUAUCACGG AUCGAAGGAA AGUAGGCGUG      50

```
GUAGCUAAAC AGCUUUGUCG ACGGG                                                    75
```

( 2 ) INFORMATION FOR SEQ ID NO:19:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
AGAUGCCUGU CGAGCAUGCU GGUGCGGCUU UGGGCGCCGU GCUUGGCGUA                          50

GCUAAACAGC UUUGUCGACG GG                                                        72
```

( 2 ) INFORMATION FOR SEQ ID NO:20:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
AGAUGCCUGU CGAGCAUGCU GGUGCGGCUU UGGGCGCCGU GCUUACGUAG                          50

CUAAACAGCU UGUCGACGG G                                                          71
```

( 2 ) INFORMATION FOR SEQ ID NO:21:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
AGAUGCCUGU CGAGCAUGCU GGUGCGGCUU UGGGCGCCGU GCUUGACGUA                          50

GCUAAACAGC UUUGUCGACG GG                                                        72
```

( 2 ) INFORMATION FOR SEQ ID NO:22:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
AGAUGCCUGU CGAGCAUGCU GGGGCGGCUU UGGGCGCCGU GCUUGACGUA                          50

GCUAAACAGC UUUGUCGACG GG                                                        72
```

( 2 ) INFORMATION FOR SEQ ID NO:23:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GGGAGAUGCC UGUCGAGCAU GCUGAGGAUC GAAGUUAGUA GGCUUUGUGU                          50

GCUCGUAGCU AAACAGCUUU GUCGACGGG                                                 79
```

( 2 ) INFORMATION FOR SEQ ID NO:24:

( i ) SEQUENCE CHARACTERISTICS:
       ( A ) LENGTH: 79 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:24:

```
GGGAGAUGCC  UGUCGAGCAU  GCUGCAUCCG  GAUCGAAGUU  AGUAGGCCGA           50

GGUGGUAGCU  AAACAGCUUU  GUCGACGGG                                    79
```

( 2 ) INFORMATION FOR SEQ ID NO:25:

( i ) SEQUENCE CHARACTERISTICS:
       ( A ) LENGTH: 79 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:25:

```
GGGAGAUGCC  UGUCGAGCAU  GCUGAUUGUU  GCGGAUCGAA  GUGAGUAGGC           50

GCUAGUAGCU  AAACAGCUUU  GUCGACGGG                                    79
```

( 2 ) INFORMATION FOR SEQ ID NO:26:

( i ) SEQUENCE CHARACTERISTICS:
       ( A ) LENGTH: 75 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:26:

```
GGGAGAUGCC  UGUCGAGCAU  GCUGGUGCGG  CUUUGGGCGC  CGUGCUUGAC           50

GUAGCUAAAC  AGCUUUGUCG  ACGGG                                        75
```